United States Patent
Shima et al.

(10) Patent No.: US 8,017,546 B2
(45) Date of Patent: Sep. 13, 2011

(54) CATALYST FOR PRODUCING ALKYLENE OXIDE, METHOD FOR PRODUCING THE SAME, AND METHOD FOR PRODUCING ALKYLENE OXIDE USING SAID CATALYST

(75) Inventors: Masahide Shima, Himeji (JP); Tadashi Sento, Himeji (JP); Masatsugu Mikawa, Kawasaki (JP); Hiroyuki Hirota, Kawasaki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 12/311,000

(22) PCT Filed: Sep. 13, 2007

(86) PCT No.: PCT/JP2007/067874
§ 371 (c)(1),
(2), (4) Date: Mar. 16, 2009

(87) PCT Pub. No.: WO2008/032797
PCT Pub. Date: Mar. 20, 2008

(65) Prior Publication Data
US 2009/0259059 A1 Oct. 15, 2009

(30) Foreign Application Priority Data

Sep. 15, 2006 (JP) .................................. 2006-250988
Sep. 28, 2006 (JP) .................................. 2006-264377

(51) Int. Cl.
*B01J 23/50* (2006.01)
*B01J 23/48* (2006.01)
*B01J 21/00* (2006.01)
*C07D 301/10* (2006.01)

(52) U.S. Cl. ......... 502/243; 502/347; 502/348; 549/534
(58) Field of Classification Search ................. 549/534; 502/243, 347, 348
See application file for complete search history.

(56) References Cited

U.S. PATENT DOCUMENTS

| 4,701,437 A | 10/1987 | Boxhoorn et al. |
| 6,153,556 A | 11/2000 | Shima et al. |
| 6,387,494 B1 | 5/2002 | Yanagida et al. |

(Continued)

FOREIGN PATENT DOCUMENTS

JP A-2002-522401 A 7/2002

(Continued)

OTHER PUBLICATIONS

Zemichael et al., Catalysis Letters, 80 (3-4), 93-98, Jun. 2002.*

(Continued)

*Primary Examiner* — Taylor Victor Oh
(74) *Attorney, Agent, or Firm* — Buchanan, Ingersoll & Rooney PC

(57) ABSTRACT

A catalyst for producing alkylene oxide including fine metal silver particles dispersed and supported on a carrier, wherein not less than 90% of the fine metal silver particles have silver particle diameters of 2 to 100 nm, is disclosed. The catalyst can be produced by impregnating a carrier with a liquid containing a silver compound or a silver ion; drying the carrier; and then irradiating the carrier with microwave to form fine metal silver particles in dispersed state on the carrier. This catalyst is used for producing olefin oxide by contact gas-phase oxidation of olefin by a molecular-oxygen-containing gas.

15 Claims, 2 Drawing Sheets

U.S. PATENT DOCUMENTS

| | | |
|---|---|---|
| 6,603,028 B1 | 8/2003 | Dorf et al. |
| 7,550,611 B2 * | 6/2009 | Xu et al. .................. 549/534 |
| 2003/0148885 A1 | 8/2003 | Weisbeck et al. |

FOREIGN PATENT DOCUMENTS

| | | |
|---|---|---|
| JP | A-62-4443 A | 1/2003 |
| JP | A-2003-13105 | 1/2003 |
| JP | A-2003-533347 A | 11/2003 |
| JP | A-2005-052838 A | 3/2005 |
| WO | WO 2005/102525 A1 | 11/2005 |

OTHER PUBLICATIONS

Kim et al., Catalysis Today, 87, (2003), 153-162.*
Jing et al., J. Sol-Gel Sci Technol (2008) 45:109-113.*

* cited by examiner

CATALYST FOR PRODUCING ALKYLENE OXIDE, METHOD FOR PRODUCING THE SAME, AND METHOD FOR PRODUCING ALKYLENE OXIDE USING SAID CATALYST

TECHNICAL FIELD

The present invention relates to a catalyst for producing alkylene oxide, method for producing the same, and method for producing alkylene oxide using said catalyst.

BACKGROUND ART

Production of ethylene oxide by contact gas-phase oxidation of ethylene with a catalyst and molecular-oxygen-containing gas has been industrially utilized widely. Although the technology has already been developed to a high level, in order to achieve further cost reduction, development of catalysts for producing ethylene oxide which exhibits superior performance in selectivity, durability, and the like has still been a research subject for researchers in this technical field.

It is well known that the performance of a catalyst for producing ethylene oxide is influenced by the size of metal silver particles supported on a carrier such as alumina, and hence trials to support metal silver as fine particles on a carrier have been done. Fact is, however, a catalyst for producing ethylene oxide comprising metal silver as fine particles supported on a carrier, which is superior in selectivity and durability and can be used industrially and advantageously, has not yet been realized.

Recently, a method for producing nano-sized fine metal particles by utilizing microwave has been proposed. For example, U.S. Pat. No. 6,387,494 B1 describes a method for producing nano-sized fine particles consisting of a metal derived from a metal salt by dissolving or dispersing the metal salt in a solvent, and then irradiating microwave thereto.

In addition, JP-A-2003-13105 describes a method for producing a carrier adhered with fine metal particles in which fine metal particles were adhered on the carrier, by mixing a solid material as carrier and a metal compound with ethylene glycol for example, and then irradiating microwave thereto.

DISCLOSURE OF INVENTION

Problem to be Solved by the Invention

However, in any of the aforementioned references, there is no specific description about a catalyst suitable for producing ethylene oxide in which a particle diameter of fine metal silver particles supported on a carrier such as alumina, particularly on a carrier having a small specific surface area of not more than 5 m²/g are in a fine range of 2 to 100 nm, that is, a catalyst for producing ethylene oxide which is superior in selectivity, durability, and the like. In addition, according to the studies by the present inventors, it was found that the method for producing fine metal particles by irradiating microwave in the presence of a solvent as described in the aforementioned references cannot produce such a catalyst for producing ethylene oxide as described above.

Thus, an object of the present invention is to provide a catalyst for producing alkylene oxide in which nano-sized fine metal silver particles are supported on a carrier such as alumina, and the catalyst is superior in selectivity, durability, and the like to conventional catalysts. Other objects are to provide a producing method thereof and a method for producing alkylene oxide using said catalyst.

Means for Solving Problem

The above objects can be attained by the following (1) to (16).

(1) A catalyst for producing alkylene oxide comprising fine metal silver particles dispersed and supported on a carrier, wherein not less than 90% of said fine metal silver particles have silver particle diameters of 2 to 100 nm.

(2) The catalyst according to the above item (1), wherein said carrier is α-alumina carrier.

(3) The catalyst according to the above item (1) or (2), wherein said carrier comprises not more than 3 mass % of silicon.

(4) The catalyst according to any one of the above items (1) to (3), wherein a supported amount of said fine metal silver particles is 3 to 40 mass % based on a mass of the carrier.

(5) The catalyst according to any one of the above items (1) to (4), wherein a supported amount of said fine metal silver particles is 3 to 25 mass % based on a mass of the carrier, and not less than 90% of the fine metal silver particles has a silver particle diameter in a range of 20 to 80 nm.

(6) The catalyst according to any one of the above items (1) to (5), wherein an average diameter of said fine metal silver particles is 10 to 100 nm.

(7) The catalyst according to any one of the above items (1) to (6), wherein a particle diameter of said fine metal silver particles are in a range of an average particle diameter ±30 nm.

(8) The catalyst according to any one of the above items (1) to (7), wherein a BET specific surface area of said carrier is 0.1 to 5.0 m²/g.

(9) The catalyst according to any one of the above items (1) to (8), wherein said carrier comprises an alkali metal element.

(10) The catalyst according to any one of the above items (1) to (9), wherein said catalyst comprises at least one element selected from a group consisting of alkali metal elements and rhenium as a promoter.

(11) The catalyst according to any one of the above items (1) to (10), wherein said carrier is 20 to 60 mass % (a water absorption rate with respect to a mass of the carrier).

(12) A method for producing a catalyst for producing alkylene oxide comprising: impregnating a carrier with a liquid containing a silver compound or a silver ion; drying the carrier; and then irradiating the carrier with microwave to form fine metal silver particles on the carrier.

(13) The method according to the above item (12), wherein the solution containing a silver compound or a silver ion further contains an amine compound.

(14) The method according to the above item (12) or (13), wherein the carrier after irradiated with microwave is treated at a temperature in a range of 400 to 950° C. in an inert gas.

(15) A method for producing alkylene oxide comprising a step of gas-phase oxidation of an olefin by molecular-oxygen-containing gas in the presence of the catalyst according to the above items (1) to (11).

(16) The method for producing alkylene oxide according to the above item (15), wherein said olefin is ethylene.

BEST MODE FOR CARRYING OUT THE INVENTION

Figure 1:
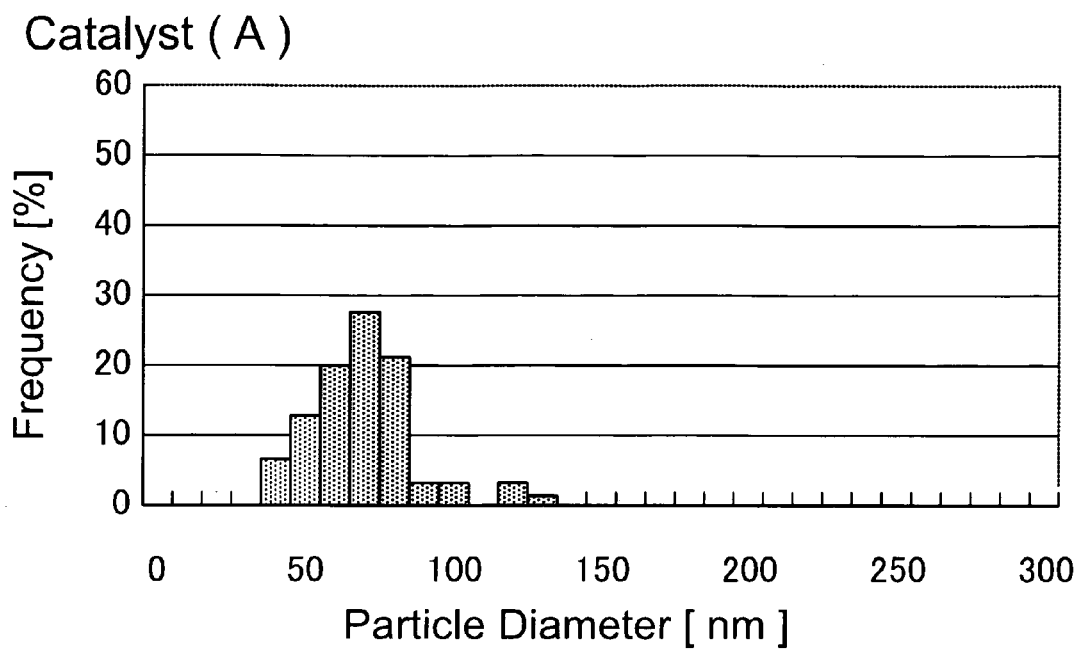
FIG. 1 shows the particle diameter distribution of fine metal silver particles in the catalyst (A) according to the present invention.

Alkylene oxide in the present invention means alkylene oxides such as ethylene oxide, 3,4-epoxy-1-butene, which are obtained by contact gas-phase oxidation of olefin compounds such as ethylene, 1,3-butadiene. Hereinafter, the present invention is explained taking ethylene oxide as an example, however, the present invention is not limited thereto.

The catalyst for producing ethylene oxide of the present invention (hereinafter, sometimes referred to as "EO catalyst") is a catalyst in which fine metal silver particles and optionally at least one element selected from cesium and rhenium are supported on a carrier such as alumina, and this constitution itself is the same as that of conventional EO catalysts. The above-mentioned carrier may be of any type so long as it can be used for producing general EO catalyst, and specifically, for example, $Al_2O_3$ (alumina), $SiO_2$ (silica), $ZrO_2$ (zirconia) and SiC (silicon carbide) are included. These are generally used alone, but may be used in combination of 2 kinds or more. Alternatively, a carrier containing these as a main component can be used. In particular, a carrier containing α-alumina as a main component is suitable. A specific surface area of the carrier is preferably 0.1 to 5 $m^2/g$, and particularly preferably 0.5 to 2 $m^2/g$. A water absorption rate of the carrier is preferably 20 to 60%, and particularly preferably 30 to 50%.

The EO catalyst of the present invention is the one in which not less than 90% of fine metal silver particles supported on the carrier have a particle diameter in a range of 2 to 100 nm, preferably 10 to 80 nm, and more preferably 20 to 60 nm. Among them, the carrier in which not less than 95% of the fine metal silver particles supported on the carrier, more preferably all of fine metal silver particles have a particle diameter in the above range is preferable. Too small particle diameter promotes complete oxidation, causing a low selectivity. Contrary, a particle diameter exceeding 100 nm is similar to known conventional EO catalysts then cannot provide a desired high selectivity and durability. An average particle diameter of said fine metal particles is 10 to 100 nm, and preferably 20 to 90 nm. Further, a particle diameter distribution of the fine metal silver particles is preferably as sharp as possible, and specifically, for example, said fine particle is preferably in a range of an average particle diameter ±30 nm, and more preferably ±20 nm. In addition, said fine metal silver particles are dispersed on the surface of carrier almost evenly.

The particle diameter of the fine metal silver particles in the present invention was measured by transmission electron microscope (JEM-100SX, manufactured by JEOL Ltd.). The sample was prepared by pulverizing the catalyst, dispersing it in water, scooping it up on a Cu-collodion membrane, and drying. Photographing was carried out at 100 kV. Particle diameter was obtained based on the photographs taken (TEM photographs) by use of a particle diameter analyzing software (Image-Pro PLUS, manufactured by Media Cybernetics Inc.).

In the EO catalyst of the present invention, the one in which the particle diameter of fine metal silver particles are in the above range as well as the amount to be supported is in a range of 3 to 40 mass %, preferably 3 to 25 mass % based on the mass of catalyst is preferable. Too small amount of the particles to be supported is not preferable due to a low catalytic activity, and too large amount is not preferable due to an increase in the catalyst cost, and the like.

Therefore, among the EO catalysts of the present invention, a catalyst, in which not less than 90% of fine metal silver particles has a particle diameter in a range of 20 to 80 nm as well as the amount of the particles to be supported is in a range of 3 to 25 mass % based on the catalyst mass, is preferable.

As a promoter, it is preferable that at least one element selected from alkali metals and rhenium is supported. Alkali metals can be used alone, but rhenium is preferably used in combination with an alkali metal. Cesium is suitable due to less deterioration in the catalytic performance. These elements are used as a form of salts of these metals, for example, nitrate salts, carbonate salts, sulfate salts, ammonium salts, oxalate salts, acetate salts, and the like, or oxides of these metals. Carbonate salts are used suitably. The amount of the promoter to be supported is not particularly limited, and it is supported with an amount in a range which is used in preparation of general EO catalysts. Specifically, for example, a range of 10 to 100,000 ppm (by mass), in particular, 100 to 10,000 ppm (by mass) is preferable. When Cesium is used, 10 to 20,000 ppm (by mass), in particular, 100 to 10,000 ppm (by mass) is preferable. A method to make the carrier support the promoter is not particularly limited, and the promoter can be supported by impregnating the carrier with or dipping in a solution thereof in water, alcohol, and the like.

The carrier contains preferably not less than 90 mass % of α-alumina, more preferably not less than 95 mass %, and further more preferably not less than 97 mass % of α-alumina. The carrier preferably contains a small amount of $SiO_2$, and the content thereof is preferably 0.1 to 5% (by mass) (by mass converted into silicon oxide to the carrier, hereinafter, the values are expressed in the same way), more preferably 0.2 to 3% (by mass), and still more preferably 0.3 to 1% (by mass). The carrier preferably contains a small amount of at least one element selected from a group consisting of alkali metals and thallium, and the content thereof is preferably 0.01 to 5% (by mass), more preferably 0.02 to 3% (by mass), and further more preferably 0.03 to 1% (by mass). As for the particle diameter of α-alumina, an α-alumina whose primary particle diameter is 0.01 to 100 μm, preferably 0.1 to 20 μm, more preferably 0.5 to 10 μm, and particularly preferably 1 to 5 μm is used. The diameter of the secondary particle is preferably 0.1 to 1,000 μm, more preferably 1 to 500 μm, further preferably 10 to 200 μm, and particularly preferably 30 to 100 μm. The BET specific surface area is preferably 0.1 to 5.0 $m^2/g$, more preferably 0.5 to 3.0 $m^2/g$, and further more preferably 0.8 to 2.0 $m^2/g$. The pore volume is 0.2 to 0.6 ml/g, and preferably 0.3 to 0.5 ml/g, and the apparent porosity is 50 to 70% (by volume), and preferably 55 to 65% (by volume).

These are measured by usual measuring methods.

These carrier may have any shape of spherical, pellet-like, ring-shaped, and the like, and preferably is ring-shaped, the equivalent diameter thereof is particularly 2 to 10 mm, and preferably 6 to 9 mm.

Next, the method for producing the EO catalyst of the present invention will be explained in detail. The method of the present invention comprises: impregnating a carrier with a liquid containing a silver compound or a silver ion; drying the carrier; and then irradiating the carrier with microwave to form fine metal silver particles on the carrier.

The aforementioned "a liquid containing a silver compound or a silver ion" means a solution or a dispersion in which a silver compound is dissolved or dispersed. As the above-mentioned silver compound, a silver compound which is generally used in preparing EO catalyst can be used. Specifically, for example, silver oxalate, silver acetate, silver nitrate, silver carbonate, silver propionate, silver lactate, silver citrate, silver neodecanoate etc. are included. Among them, silver oxalate and silver acetate are suitably used.

As the aforementioned solvent, any solvent may be used so long as the solvent can dissolve or disperse the above-mentioned silver compounds, and usually water is used. Therefore, as the aforementioned "a liquid containing a silver compound or a silver ion" (hereinafter, sometimes referred to as "impregnating liquid"), a liquid in which silver oxalate or silver acetate is dissolved or dispersed is generally used. The concentration of silver oxalate or silver acetate in this liquid may be arbitrarily determined by taking account of the amount of fine metal silver particles to be supported, and the like.

The above impregnating liquid preferably further contains an amine compound. As the above-mentioned amine compound, an amine compound which is generally used in preparing EO catalysts can be used. Specifically, ammonia; monoamine such as pyridine, butylamine; alkanolamine such as monoethanolamine, diethanolamine, triethanolamine; polyamine such as ethylenediamine, propylenediamine, butylenediamine; and the like are included. Among them, monoethanolamine and ethylenediamine are suitably used.

Amount of the amine compound to be added is preferably an equimolar amount to the silver compound for example so that the silver compound and the amine compound form a complex. By forming a complex between the silver compound and the amine compound, the impregnating liquid becomes a solution state then the impregnation work can proceed easily.

Thus, as the above-mentioned impregnating liquid, a liquid in which a silver compound such as silver nitrate, silver oxalate, silver acetate and an amine compound such as ethanolamine, ethylenediamine, propylenediamine are dissolved in water is suitably used.

According to the present invention, the carrier is impregnated into the above-mentioned impregnating liquid, the impregnating liquid is dried, and then the carrier is irradiated with microwave. It is important to dry the impregnating liquid before irradiated with microwave, and irradiation of microwave without drying cannot achieve the aimed catalyst.

Generally, when a silver ion is reduced in a solvent to form fine silver particles, stable particles are formed through two steps, that is, particle nucleus formation and particle growth. According to the present invention, it is understood that fine particles are formed because many particle nuclei concurrently generates because of the rapid heating by microwave on the molecular level and hence growth of these particles is extremely inhibited. However, it should be noted that the present invention is not constrained in any way by such theoretical consideration.

A method for drying the above impregnating liquid is not particularly limited, and the drying can be done in the stream of at least one kind of gas selected from inert gases such as air, nitrogen, helium, or a mixed gas of 2 or more kinds. The temperature may be at 30 to 200° C., preferably 50 to 150° C. for 0.01 to 100 hours, preferably 0.05 to 10 hours. The drying can be suitably done in the nitrogen gas stream at a temperature of 80 to 150° C. for 0.01 to 100 hours.

As an microwave irradiation device, specialized devices are commercially available, but devices for domestic use may be used.
(Irradiation Conditions)
Frequency: 2.45 GHz
Irradiation time: 1 second to 8 hours
Intensity range of microwave: 0.001 to 5 W/cm$^3$ By irradiating with appropriately setting the aforementioned irradiation time and intensity of microwave, fine metal silver particles having the aforementioned particle diameter can be formed. Higher intensity makes treatment time shorter.

Next, specific method for preparing EO catalyst supported by fine metal silver particles and cesium metal on a carrier will be explained.

One method is used in the case that the aforementioned impregnating liquid does not contain an amine compound. This method comprises: impregnating a carrier with an impregnating liquid; drying the carrier; and then irradiating the carrier with microwave to form fine metal silver particles on the carrier; thereafter contacting the carrier supporting the fine metal silver particle with a cesium solution; and drying. As the above-mentioned cesium solution, a solution which is generally used for preparing EO catalysts can be used. Specifically, for example, a solution of cesium compound such as cesium nitrate, cesium carbonate, cesium chloride, dissolved in alcohol such as methanol, ethanol, ethylene glycol or water can be used. The concentration of the cesium compound can be appropriately determined by taking account of the amount of cesium metal to be supported, and the like.

Another method uses an impregnating liquid containing a silver compound and an amine compound. The method comprises: impregnating a carrier with this impregnating liquid; drying; and then irradiating the carrier with microwave to form fine metal silver particles on the carrier; thereafter washing the carrier supporting the fine metal silver particle with water; contacting the carrier with a cesium solution; and drying. In this method, it is necessary to remove residual amine compound by washing with water before contacting the carrier supporting fine metal silver particles with the cesium solution. If the carrier supporting fine metal silver particles is contacted with the cesium solution without removing the residual amine compound by washing with water, the desired amount of cesium metal cannot be supported on the carrier.

The above-mentioned body supporting the fine metal silver particles is preferably further treated in an inert gas atmosphere. Treatment temperature is 400 to 950° C., and further preferably 500 to 700° C., and treatment time is 0.1 to 10 hours, and further preferably 1 to 5 hours. The aforementioned inert gas atmosphere includes an inert gas atmosphere selected from nitrogen, helium, argon, and the like; a reducing gas atmosphere selected from hydrogen, carbon monoxide, and the like; or a mixed gas atmosphere of an inert gas and a reducing gas.

Specifically, for example, the above-mentioned catalyst for producing ethylene oxide is contacted with a raw gas, which comprises 0.5 to 40 volume % of ethylene, 3 to 10 volume % of oxygen, 5 to 30 volume % of carbon dioxide, and the remainder of inert gas such as nitrogen, argon, steam, and of lower hydrocarbons such as methane, ethane, and further contains a halogenated organic compound such as ethylene dichloride, ethyl chloride as a reaction retarder. The conditions at the contact are a space velocity of 1,000 to 30,000 hr$^{-1}$ (STP), preferably 3,000 to 8,000 hr$^{-1}$ (STP), a pressure of 0.2 to 4 MPa, preferably 1.5 to 4 MPa (gauge left), and a temperature of 180 to 300° C., preferably 200 to 260° C.

In the above-mentioned remainder gas, a content of ethane is preferably 0.01 to 3 volume %, and further suitably 0.1 to 0.5 volume %.

In the above-mentioned remainder gas, a content of halogenated organic compound is preferably 0.1 to 100 ppm, and suitably 1 to 10 ppm.

It should be noted that the conversion rate and selectivity described in the Examples and Comparative Examples were calculated by the following mathematical expressions.

$$\text{Conversion rate (\%)} = \frac{\left(\begin{array}{c}\text{mole number of}\\\text{reacted ethylene}\end{array}\right)}{\left(\begin{array}{c}\text{mole number of}\\\text{ethylene in raw gas}\end{array}\right)} \times 100 \quad \text{[Mathematical Expression 1]}$$

$$\text{Selectivity(\%)} = \frac{\left(\begin{array}{c}\text{mole number of ethylene}\\\text{converted to ethylene oxide}\end{array}\right)}{\left(\begin{array}{c}\text{mole number of}\\\text{reacted ethylene}\end{array}\right)} \times 100$$

EXAMPLES

Next, the present invention will be explained in more detail referring to Examples.

Through this specification, numerical values of each property were measured by the following methods.

(1) Quantitative Determination of $SiO_2$ and $Na_2O$ Components:

These amounts were measured by fluorescent X-ray analysis.

(2) Specific Surface Area:

The carrier was crushed and classified to a fraction having a particle diameter of 0.85 to 1.2 mm. Around 0.2 g of the classified carrier was correctly weighed. The sample was degassed at 200° C. for at least 30 minutes, thereafter a specific surface area was measured according to the BET (Brunauer-Emett-Teller) method (the method described in Journal of the American Chemical Society, Vol. 60, item 309-316 (1938)).

(3) Water Absorption Rate:

Referring to the method of Japanese Industrial Standards (JIS R 2205-(1998)), the rate was measured by the following method.

a) The uncrushed carrier (ring-shaped, spherical, and the like) was put in a dryer at 120° C. After reaching a constant mass, the carrier was weighed (Dry Sample Weight: W1 (g)).

b) The weighed carrier with submerged under water was boiled for not less than 30 minutes, thereafter cooled in water at room temperature. This was taken as a water-saturated sample.

c) The water-saturated sample was taken up from water, wiped off quickly with wet cloth to remove water drops on the surface, thereafter weighed (Water-Saturated Sample weight: W2 (g)).

d) The water absorption rate was calculated according to the following mathematical expression.

Water absorption rate=$((W2-W1)/W1)\times 100$      [Mathematical Expression 2]

Example 1

54.4 g of a ring-shaped carrier whose main component was α-alumina, equivalent diameter was 8 mm, (specific surface area: 0.7 m²/g, water absorption rate: 42%) was impregnated with a silver-containing liquid including 20 g of silver oxalate, 8 ml of monoethanolamine and 10 g of water, then, the carrier was dried at 120° C. for 3 hours to remove the liquid component. This carrier was placed in a commercially available microwave oven (1,000 W INVERTER, manufactured by SHARP Corp.), irradiated with microwave (2.45 GHz, 0.3 W/cm³) for 5 minutes, and washed with water to obtain bodies supporting fine metal silver particles. Thereafter, these bodies supporting fine metal silver particles was dipped into a solution of 0.4 g of cesium carbonate in 75 ml of ethanol, then the bodies were dried at 30° C. for 18 hours in the nitrogen gas stream, resulting in catalyst (A).

The particle diameter of fine metal silver particles of the thus obtained catalyst (A) was measured by a transmission electron microscope (JEM-100SX, manufactured by JEOL Ltd.). The sample was prepared by pulverizing the catalyst, dispersing it in water, scooping it up on a Cu-collodion membrane, and drying. Photographing was carried out at 100 kV. The particle diameter was obtained based on the photographs taken (TEM photographs) by use of a particle diameter analyzing software (Image-Pro PLUS, manufactured by Media Cybernetics Inc.). Particle diameter distribution of the fine metal silver particles in catalyst (A) is shown in FIG. 1. Not less than 90% of the fine metal silver particles had particle diameters in a range of 20 to 80 nm, and their average particle diameter was 61 nm. The amount of the fine metal silver particles supported was 20.1 mass %.

For this catalyst (A), catalytic performance for producing ethylene oxide by contact gas-phase oxidation of ethylene was evaluated by the following method.

<Evaluation of Catalytic Performance>

Catalyst (A) was crushed and classified to a fraction having an average particle diameter of 600 to 850 μm. 1.2 g of this fraction of catalyst (A) was packed in a double-tube type stainless reactor whose inside diameter was 3 mm, tube length was 300 mm, and whose system was external heating type. Through this packed layer, a gas consisting of 25 volume % of ethylene, 7 volume % of oxygen, 3 ppm of ethylene dichloride, and the remainder including methane, nitrogen, argon and ethane was introduced. The reaction was conducted under the conditions of a reaction pressure of 20 kg/cm²·G and a space velocity of 11,000 hr⁻¹, so that the conversion rate of ethylene reached 10 volume %. Results after 5 days and after 30 days from the start of the reaction are shown in Table 1.

Example 2

54.4 g of a ring-shaped carrier whose main component was α-alumina and dimension was the same as that in Example 1 (specific surface area: 2.0 m²/g, water absorption rate: 38% was) impregnated with a silver-containing liquid consisting of 5 g of silver oxalate, 3 ml of ethylenediamine and 4 g of water. Thereafter, the carrier was dried at 120° C. for 3 hours to remove the liquid component. The carrier was placed in the same microwave oven as that used in Example 1, irradiated with microwave (2.45 GHz, 0.3 W/cm³) for 5 minutes, and washed with water to obtain bodies supporting fine metal silver particles. These bodies supporting fine metal silver particles were dipped into a solution of 0.4 g of cesium carbonate in 75 ml of ethanol, then the bodies were dried at 30° C. for 18 hours in the nitrogen gas stream, resulting in catalyst (B).

Figure 2:
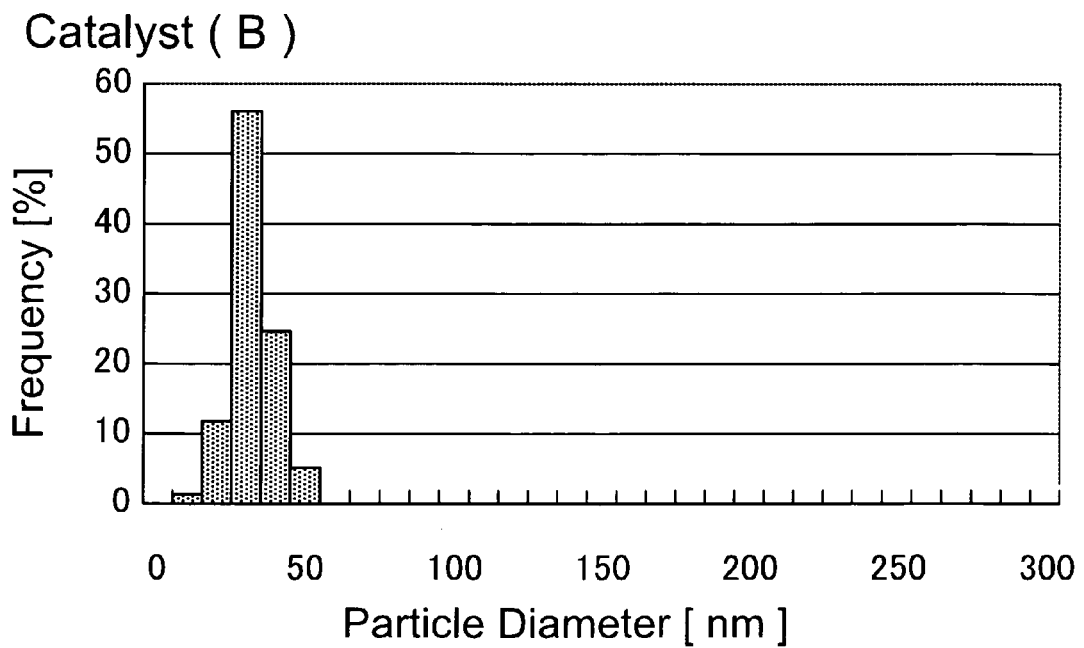
FIG. 2 shows the particle diameter distribution of fine metal silver particles in the catalyst (B) according to the present invention.

The particle diameter distribution of the fine metal silver particles in catalyst (B) is shown in FIG. 2. Not less than 95% of the fine metal silver particles had a particle diameter in a range of 20 to 80 nm, and the average particle diameter thereof was 31 nm. The amount of the fine metal silver particles supported was 5.8 mass %.

For this catalyst (B), the catalytic performance for producing ethylene oxide by catalytic gas-phase oxidation of ethylene was evaluated in the similar way to in Example 1. The results are shown in Table 1.

Comparative Example 1

54.4 g of q ring-shaped carrier whose main component was α-alumina and dimension was the same as that in Example 1, (specific surface area was 2.3 m²/g, and water absorption rate was 47%) was impregnated with a silver-containing liquid consisting of 20 g of silver oxalate, 8 ml of monoethanolamine and 10 g of water. This carrier was placed in the same microwave oven as that used in Example 1 directly without removing the liquid component by drying in the nitrogen gas stream, and irradiated with microwave (2.45 GHz, 0.3 W/cm³) for 5 minutes. After that, a silver mirror film was formed on the outside of the carrier, and aggregation of particles was observed. These silver supporting bodies were washed with water, they were dipped into a solution of 0.4 g of cesium carbonate in 75 ml of ethanol for 2 hours, then they were dried at 30° C. for 18 hours in the nitrogen gas stream, resulting in catalyst (X).

Figure 3:
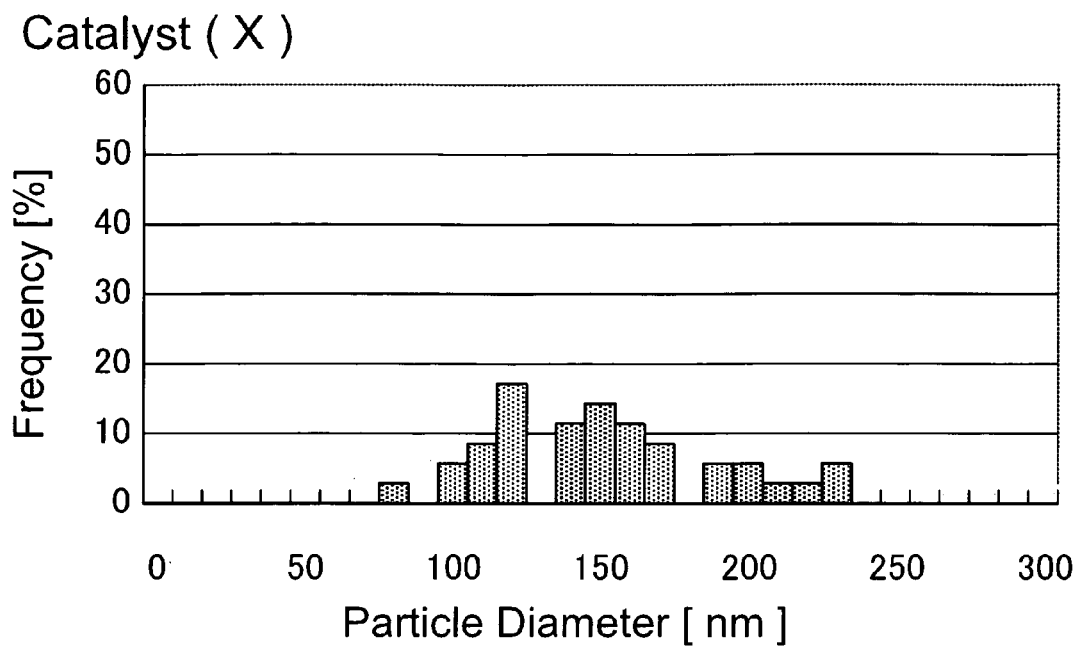
FIG. 3 shows the particle diameter distribution in the conventional catalyst (X).

The particle diameter distribution of the fine metal silver particles in catalyst (X) is shown in FIG. 3. Not less than 90% of the fine metal silver particles had a particle diameter in a range of 100 to 220 nm, and the average particle diameter thereof was 150 nm. The supported amount of the fine metal silver particles was 19.9 mass %.

For this catalyst (X), the catalytic performance for producing ethylene oxide by contact gas-phase oxidation of ethylene was evaluated in the same way as in Example 1. The results are shown in Table 1.

Comparative Example 2

54.4 g of a ring-shaped carrier whose main component was α-alumina and dimension was the same as that in Example 1 (specific surface area was 2.5 m²/g, and water absorption rate was 48%) was impregnated with a silver-containing liquid consisting of 20 g of silver oxalate, 8 ml of monoethanolamine and 10 g of water. The carrier was dried in the nitrogen gas stream to remove the liquid component, then the carrier was heat-treated in air at 400° C. for 5 minutes to obtain carriers supporting silver. These carriers supporting silver were washed with water, then dipped into a solution of 0.4 g of cesium carbonate in 75 ml of ethanol for 2 hours, thereafter the carriers were dried at 30° C. for 18 hours in the nitrogen gas stream, resulting in catalyst (Y).

Figure 4:
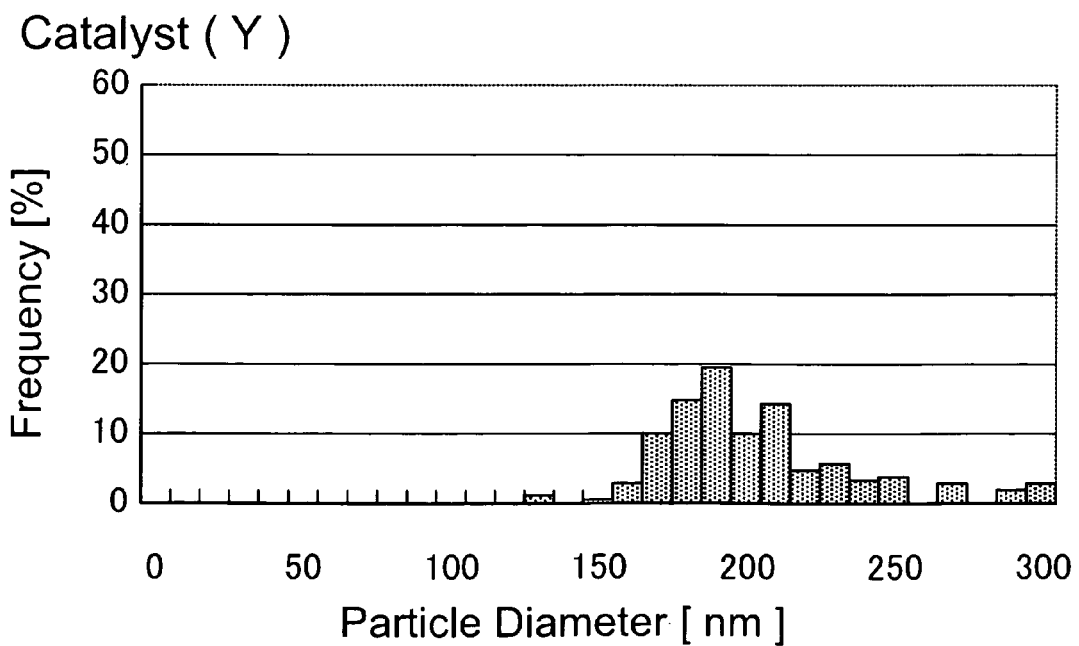
FIG. 4 shows the particle diameter distribution in the conventional catalyst (Y).

The particle diameter distribution of the fine metal silver particles in catalyst (Y) is shown in FIG. 4. The average particle diameter of the fine metal silver particles was 205 nm. The supported amount of the fine metal silver particles was 20.3 mass %.

For this catalyst (Y), the catalytic performance for producing ethylene oxide by contact gas-phase oxidation of ethylene was evaluated in the same way to in Example 1. The results are shown in Table 1.

TABLE 1

| Catalyst | After 5 days | | After 30 days | |
|---|---|---|---|---|
| | Reaction Temperature (° C.) | Selectivity (%) | Reaction Temperature (° C.) | Selectivity (%) |
| (A) | 241 | 80.5 | 243 | 80.6 |
| (B) | 239 | 81.0 | 240 | 81.0 |
| (X) | 244 | 80.0 | 249 | 79.5 |
| (Y) | 245 | 79.2 | 249 | 78.5 |

Example 3

54.4 g of a ring-shaped carrier whose main component was α-alumina and dimension was the same as that in Example 1 (specific surface area: 1.7 m²/g, water absorption rate: 42%, Na₂O content: 0.04 mass %) was impregnated with a silver-containing liquid consisting of 15 g of silver oxalate, 8 ml of monoethanolamine and 10 g of water, then the liquid component was removed by drying at 120° C. for 3 hours. These carriers were placed in a commercially available microwave oven (1,000 W INVERTER, manufactured by SHARP Corp.), irradiated with microwave (2.45 GHz, 0.3 W/cm³) for 5 minutes, and then washed with water to obtain catalyst precursors supporting fine metal silver particles. Thereafter, the catalyst precursors supporting fine metal silver particles were dipped into a solution of 0.2 g of cesium carbonate in 75 ml of ethanol, then the bodies were dried at 30° C. for 18 hours in the nitrogen gas stream. The bodies were heat-treated at 600° C. for 3 hours in the nitrogen gas stream, resulting in catalyst (C).

In catalyst (C), not less than 90% of the fine metal silver particles had a particle diameter in a range of 38 to 99 nm, and their average particle diameter was 69 nm. The supported amount of the fine metal silver particles was 15.0 mass %, and the content of silica was 0.5 mass %.

For this catalyst (C), the catalytic performance for producing ethylene oxide by contact gas-phase oxidation of ethylene was evaluated by the following method.

<Evaluation of Catalytic Performance>

Catalyst (C) was crushed and classified to a fraction having an average particle diameter of 600 to 850 μm. 1.2 g of the catalyst (C) was packed in a double-tube type stainless reactor whose inside diameter was 3 mm, tube length was 300 mm, and system was an external heating type. A gas consisting of 25 volume % of ethylene, 7 volume % of oxygen, 3 ppm of ethylene dichloride, and the remainder including methane, nitrogen, argon and ethane was introduced into this packed layer. The reaction was carried out under the conditions of reaction pressure of a 20 kg/cm²·G and a space velocity of 22,000 hr⁻¹, so that the conversion rate of ethylene reached 12 volume %. The results after 30 days and after 110 days from the start of the reaction are shown in Table 2.

Example 4

54.4 g of a ring-shaped carrier whose main component was α-alumina, dimension was the same as that in Example 1, (specific surface area: 1.3 m²/g, water absorption rate: 40%, Na₂O content: 0.2 mass %) was impregnated with a silver-containing liquid consisting of 15 g of silver oxalate, 8 ml of monoethanolamine and 10 g of water, then the liquid component was removed by drying at 120° C. for 3 hours. These carriers were placed in the same microwave oven as that used in Example 1, irradiated with microwave (2.45 GHz, 0.3

W/cm$^3$) for 5 minutes, and washed with water to obtain bodies supporting fine metal silver particles. Thereafter, the bodies supporting fine metal silver particles were dipped into a solution of 0.4 g of cesium carbonate in 75 ml of ethanol, then they were dried at 30° C. for 18 hours in the nitrogen gas stream. The bodies were further heat-treated at 600° C. for 3 hours in the nitrogen gas stream, resulting in catalyst (D).

In catalyst (D), not less than 90% of the fine metal silver particles had a particle diameter in a range of 19 to 98 nm, and the average particle diameter thereof was 68 nm. The supported amount of fine metal silver particles was 15.0 mass %, and the content of silica was 1.9 mass %.

For this catalyst (D), the catalytic performance for producing ethylene oxide by contact gas-phase oxidation of ethylene was evaluated in the same way as in catalyst (C).

TABLE 2

| | Reaction days | | | |
|---|---|---|---|---|
| | After 30 days | | After 110 days | |
| | Reaction Temperature (° C.) | Selectivity (%) | Reaction Temperature (° C.) | Selectivity (%) |
| Catalyst (C) | 265 | 79.1 | 264 | 79.1 |
| Catalyst (D) | 261 | 78.5 | 268 | 77.8 |

INDUSTRIAL APPLICABILITY

The catalyst of the present invention exhibits an excellent performance in contact gas-phase oxidation of, olefin by molecular-oxygen-containing gas for example, because the fine metal silver particles having a particle diameter in the specific range are supported almost evenly. In particular, the invention is suitable for producing ethylene oxide by catalytic gas-phase oxidation of ethylene, and can produce ethylene oxide with high selectivity. In addition, since sintering of the fine metal silver particles hardly occurs, the catalyst shows high durability, and allows stable contact gas-phase oxidation of ethylene over a long period. Because, minute fine metal silver particles are supported, the supported amount can be reduced compared with those in conventional catalysts.

According to the method for producing the catalyst for producing alkylene oxide of this invention, a catalyst, which supports nano-sized fine metal silver particles and is suitable for producing an alkylene oxide by gas-phase oxidation of a corresponding olefin, in particular, for producing ethylene oxide by gas-phase oxidation of ethylene, can be efficiently produced. By this method, the silver can be evenly supported as nano-sized fine particles, and as a result, the catalyst for producing ethylene oxide, in which sintering of silver hardly occurs during use, can be obtained.

What is claimed is:

1. A catalyst for producing alkylene oxide comprising fine metal silver particles dispersed and supported on a carrier, wherein not less than 90% of said fine metal silver particles have a silver particle diameter of 2 to 100 nm, wherein an average diameter of said fine metal silver particles is 30 to 100 nm, and wherein a water absorption rate of the carrier is 20 to 60%.

2. The catalyst according to claim 1, wherein said carrier is an α-alumina carrier.

3. The catalyst according to claim 1, wherein said carrier comprises silicon oxide in an amount of 0.1 to 5% by mass.

4. The catalyst according to claim 1, wherein a supported amount of said fine metal silver particles is 3 to 40 mass % based on a mass of the carrier.

5. The catalyst according to claim 1, wherein a supported amount of said fine metal silver particles is 3 to 25 mass % based on a mass of the carrier, and not less than 90% of the fine metal silver particles has a silver particle diameter in a range of 20 to 80 nm.

6. The catalyst according to claim 1, wherein particle diameters of said fine metal silver particles are in a range of 30 nm less than the average particle diameter to 30 nm greater than the average particle diameter.

7. The catalyst according to claim 1, wherein a BET specific surface area of said carrier is 0.1 to 5.0 m$^2$/g.

8. The catalyst according to claim 1, wherein said carrier comprises an alkali metal element.

9. The catalyst according to claim 1, wherein said catalyst comprises at least one element selected from the group consisting of alkali metals and rhenium as a promoter.

10. The catalyst according to claim 1, wherein a water absorption rate with respect to a mass of said carrier is 20 to 60 mass %.

11. A method for producing a catalyst for producing alkylene oxide comprising: impregnating a carrier with a liquid containing a silver compound or a silver ion; drying the carrier; and then irradiating the carrier with microwave to form fine metal silver particles on the carrier.

12. The method according to claim 11, wherein the solution containing a silver compound or a silver ion further contains an amine compound.

13. The method according to claim 11, wherein the carrier after being irradiated with microwave is treated at a temperature in a range of 400 to 950° C. in an inert gas.

14. A method for producing alkylene oxide comprising conducting a step of gas-phase oxidation of an olefin by a molecular-oxygen-containing gas in the presence of the catalyst according to claim 1.

15. The method for producing alkylene oxide according to claim 14, wherein said olefin is ethylene.

* * * * *